United States Patent
Bafkar et al.

(10) Patent No.: US 12,211,209 B2
(45) Date of Patent: Jan. 28, 2025

(54) PREDICTION AND INTERVENTION OF OBSTRUCTIVE SLEEP APNOEA

(71) Applicant: COMMONWEALTH SCIENTIFIC AND INDUSTRIAL RESEARCH ORGANISATION, Australian Capital Territory (AU)

(72) Inventors: Omid Bafkar, Victoria (AU); Vu Thua Nguyen, Victoria (AU); Gary Rosengarten, Victoria (AU); Ivan Stuart Cole, Victoria (AU); Stefan Gulizia, Victoria (AU)

(73) Assignee: Commonwealth Scientific and Industrial Reseach Organisation, Campbell (AU)

( * ) Notice: Subject to any disclaimer, the term of this patent is extended or adjusted under 35 U.S.C. 154(b) by 0 days.

(21) Appl. No.: 17/612,696

(22) PCT Filed: May 20, 2020

(86) PCT No.: PCT/AU2020/050494
§ 371 (c)(1),
(2) Date: Nov. 19, 2021

(87) PCT Pub. No.: WO2020/232502
PCT Pub. Date: Nov. 26, 2020

(65) Prior Publication Data
US 2022/0222823 A1    Jul. 14, 2022

(30) Foreign Application Priority Data
May 20, 2019    (AU) ................. 2019901697

(51) Int. Cl.
*G06T 15/00*    (2011.01)
*G06T 7/00*     (2017.01)
(Continued)

(52) U.S. Cl.
CPC ............ *G06T 7/0016* (2013.01); *G06T 17/20* (2013.01); *G06T 19/20* (2013.01); *G16H 30/40* (2018.01);
(Continued)

(58) Field of Classification Search
CPC ... A61B 5/4836; A61B 5/7264; A61B 5/4818; A61B 5/055; A61B 5/0826; A61B 6/032;
(Continued)

(56) References Cited

U.S. PATENT DOCUMENTS

| 8,929,623 | B2 * | 1/2015 | Hsiao | ................. G06T 7/0012 600/533 |
| 11,432,742 | B2 * | 9/2022 | Iwasaki | ................. G16H 50/50 |

(Continued)

FOREIGN PATENT DOCUMENTS

| WO | 2016/006633 A1 | 1/2016 |
| WO | 2018/159759 A1 | 9/2018 |

OTHER PUBLICATIONS

Iwasaki T, Saitoh I, Takemoto Y, Inada E, Kanomi R, Hayasaki H, Yamasaki Y. Evaluation of upper airway obstruction in Class II children with fluid-mechanical simulation. American Journal of Orthodontics and Dentofacial Orthopedics. Feb. 1, 2011;139(2):e135-45.*

(Continued)

*Primary Examiner* — Phu K Nguyen
(74) *Attorney, Agent, or Firm* — Kilpatrick Townsend & Stockton

(57) ABSTRACT

Described herein are systems and methods for the simulation of the upper airway of a subject. One embodiments provides a method (100) including the initial step (101) of receiving one or more tomographic images of the subject. At step (102) a three dimensional geometric model of the upper airway is generated from the one or more tomographic
(Continued)

images. The geometric model includes a network of interconnected deformable mesh elements collectively defining a fluid domain (310) and a solid domain (320). The solid domain (320) defining a single unitary model of the entire upper airway region segmented into a plurality of predefined geometric regions, each being defined by one or more common anatomical parameters. At step (103), a computer simulation is performed on the geometric model to simulate behaviour of the upper airway when the subject is positioned in a predefined position. The computer simulation includes (103*a*) performing a Computational Fluid Dynamics (CFD) analysis on the fluid domain and then (103*b*) performing a Fluid-Structure Interaction (FSI) analysis between the fluid and solid domains under the influence of an applied gravity effect. Finally, at step (104), subject-specific parameters are output which are indicative of the behaviour of the upper airway.

23 Claims, 13 Drawing Sheets

(51) Int. Cl.
| | | |
|---|---|---|
| *G06T 17/20* | (2006.01) | |
| *G06T 19/20* | (2011.01) | |
| *G16H 30/40* | (2018.01) | |
| *G16H 50/30* | (2018.01) | |
| *G16H 50/50* | (2018.01) | |
| *A61B 5/00* | (2006.01) | |

(52) U.S. Cl.
CPC .............. *G16H 50/30* (2018.01); *G16H 50/50* (2018.01); *A61B 5/4848* (2013.01); *G06T 2207/10072* (2013.01); *G06T 2207/20081* (2013.01); *G06T 2207/30004* (2013.01); *G06T 2210/24* (2013.01); *G06T 2210/41* (2013.01)

(58) Field of Classification Search
CPC ...... A61B 5/4848; G16H 30/40; G16H 50/30; G16H 50/50; G06F 30/27; G06F 30/28; G06T 2210/41; G06T 2207/30004; G06T 17/20; G06T 7/0016; G06T 19/20; G06T 7/0012; G06T 2207/30061; G06T 2207/10081; G06T 2219/2021; G06T 2210/24; G06T 2207/20081

USPC .......................................................... 345/418
See application file for complete search history.

(56) References Cited

U.S. PATENT DOCUMENTS

| | | |
|---|---|---|
| 2007/0255161 A1 | 11/2007 | De Backer |
| 2011/0093243 A1 | 4/2011 | Tawhai et al. |
| 2011/0293156 A1* | 12/2011 | Hsiao ..................... G06T 7/62 |
| | | 382/128 |
| 2015/0351714 A1 | 12/2015 | De Backer |
| 2017/0329927 A1 | 11/2017 | Taherian et al. |
| 2020/0060579 A1 | 2/2020 | Iwasaki et al. |

OTHER PUBLICATIONS

Iwasaki T, Takemoto Y, Inada E, Sato H, Suga H, Saitoh I, Kakuno E, Kanomi R, Yamasaki Y. The effect of rapid maxillary expansion on pharyngeal airway pressure during inspiration evaluated using computational fluid dynamics. International journal of pediatric otorhinolaryngology. Aug. 1, 2014;78(8):1258-64.*

Maspero C, Giannini L, Galbiati G, Rosso G, Farronato G. Obstructive sleep apnea syndrome: a literature review. Minerva Stomatol. Apr. 1, 2015;64(2):97-109.*

Suga H, Iwasaki T, Mishima K, Nakano H, Ueyama Y, Yamasaki Y. Evaluation of the effect of oral appliance treatment on upper-airway ventilation conditions in obstructive sleep apnea using computational fluid dynamics. CRANIO®. Mar. 31, 2019.*

Henrik Strand Moxness M, Wülker F, Helge Skallerud B, Nordgård S. Simulation of the upper airways in patients with obstructive sleep apnea and nasal obstruction: A novel finite element method. Laryngoscope Investigative Otolaryngology. Apr. 2018;3(2):82-93.*

International Search Report and Written Opinion received for International Appl. PCT/AU2020/050494, mailed Jul. 10, 2020, 10 pages.

Chouly et al., "Numerical and experimental study of expiratory flow in the case of major upper airway obstructions with fluid-structure interaction", Journal of Fluids and Structures, vol. 24, No. 2,, Oct. 17, 2007, 250-269.

EP 20809523.2, "European Search Report", May 12, 2023, 7 pages.
Wang et al., "Numerical Analysis of Respiratory Flow patterns within human upper airway", ACTA Mechanics Sinica, vol. 25, No. 6,, Aug. 19, /2009, 737-746.

* cited by examiner

PREDICTION AND INTERVENTION OF OBSTRUCTIVE SLEEP APNOEA

CROSS-REFERENCE TO RELATED APPLICATIONS

This application is a 371 U.S. National Phase Application of International Patent Application No. PCT/AU2020/050494, filed May 20, 2020, which claims priority to Australian Application No. 2019901697, filed May 20, 2019, which are herein incorporated by reference in their entirety for all purposes.

TECHNICAL FIELD

The present invention relates to study of the behaviour of the upper airway of subjects and in particular to systems and methods for the simulation of the upper airway for diagnosis and treatment of upper airway-related conditions in humans such as Obstructive Sleep Apnoea.

While some embodiments will be described herein with particular reference to that application, it will be appreciated that the invention is not limited to such a field of use, and is applicable in broader contexts.

BACKGROUND OF INVENTION

Obstructive Sleep Apnoea (OSA) is a common disease. Fatigue, headache, and sleepiness are some of the main symptoms of OSA, which causes low blood oxygen levels, and consequently, can lead to stroke, pulmonary disease, uncontrollable hypertension and possibly death. The main causes of OSA are size restrictions of upper airway anatomy, poor neuromuscular control and obesity.

Polysomnography (PSG), which is commonly referred to as a 'sleep study', is the current gold standard for diagnosing OSA. However, while PSG is able to detect and characterise the severity of OSA, it does not provide any detail about the specific cause of the obstruction initiating airway collapse.

To better understand the airflow behaviour along the upper airway, some recent modelling studies have utilised computational fluid dynamics (CFD) to simulate air flowing through the upper airway. Although, CFD can provide the flow behaviour, it cannot deliver information regarding the deformation caused by airflow which, in turn, changes the flow behaviour. More recent studies have included fluid-structure interaction (FSI) into the modelling. FSI simulates interactions between fluid flows and surrounding structures. For example, see Liu, Y et al. "*Study of the upper airway of obstructive sleep apnea patient using fluid structure interaction*", Respiratory Physiology & Neurobiology, Vol. 240: 54-61, February 2018, doi: 10.1016.

However, while current numerical modelling techniques involving FSI are promising, it remains challenging to accurately predict the deformation of the airway during breathing cycles, and thus predict the occurrence of OSA or even ascertain the efficacy of treatment regimes.

US Patent Application Publication 2020/0060579 A1 by Tomonori et al. ("Tomonori") entitled "Airway ventilation state calibration system and system for predicting airway deformation during sleep" teaches using digital image data such as CT images to generate a model of a patient's nasal cavity region and simulating the patient's breathing cycle using fluid-structure coupled analysis. Tomonori also models other regions of the upper airway system but these are modelled separately to the nasal cavity. Furthermore, Tomonori requires the nasal cavity model to be a rigid body during the nasal cavity model generation. These limitations restrict the ability to realistically model the upper airway of a patient.

The discussion of the background to the invention included herein including reference to documents, acts, materials, devices, articles and the like is included to explain the context of the present invention in light of the inventors' knowledge. This is not to be taken as an admission or a suggestion that any of the material referred to was published, known or part of the common general knowledge in Australia or in any other country as at the priority date of any of the claims.

SUMMARY OF INVENTION

One aspect of the present invention provides a method of simulating behaviour of an upper airway of a subject, the method including the steps:
  receiving one or more tomographic images of the subject, the image including the patient's upper airway region captured at a predefined breathing state;
  generating, from the one or more tomographic images, a three dimensional geometric model of the upper airway, the geometric model including a network of interconnected deformable mesh elements collectively defining:
    a fluid domain indicative of an interior of the upper airway region through which fluids are able to flow; and
    a solid domain indicative of an exterior of the upper airway region, the solid domain defining a single unitary model of the entire upper airway region segmented into a plurality of predefined geometric regions, each predefined geometric region being defined by one or more common anatomical parameters;
  performing a computer simulation on the geometric model to simulate behaviour of the upper airway when the subject is positioned in a predefined position, the computer simulation including:
    performing a Computational Fluid Dynamics (CFD) analysis on the fluid domain;
    performing a Fluid-Structure Interaction (FSI) analysis between the fluid and solid domains under the influence of an applied gravity effect at a predefined direction through the geometric model corresponding to the predefined position; and
  outputting subject-specific parameters indicative of the behaviour of the upper airway.

In some embodiments, the method includes the step of assessing the subject's likelihood of a sleep disorder from the subject-specific parameters. In some embodiments, the sleep disorder is Obstructive Sleep Apnoea.

In some embodiments, the method includes the step of assessing the subject's response to a treatment regimen from the subject-specific parameters.

In some embodiments, the predefined geometric regions include a tongue region having an associated mass anatomical parameter.

In some embodiments, the anatomical parameters include tissue stiffness.

In some embodiments, the predefined geometric regions include one or more of the trachea, cricoid cartilage, soft palate, nasopharynx, nasal cavities.

In some embodiments, the anatomical parameters include tissue density. In some embodiments, the anatomical parameters include a shape of a geometric region. In some embodiments, the anatomical parameters include a size of a geometric region.

In some embodiments, the predefined position includes a prone laying position, a supine laying position, a lateral left laying position, a lateral right laying position or a seated position.

The tomographic images preferably include CT images.

In some embodiments, the method according to the first aspect includes the step of outputting a graphical representation of a simulated breathing cycle of the patient.

In some embodiments, the behaviour of the upper airway includes a breathing performance of the subject.

In some embodiments, the subject-specific parameters include an Apnoea-Hypopnea Index (AHI, a peak volume flow rate of subject breathing, an average breathing rate of the subject and/or a value or range of values indicative of upper airway closure or displacement.

In some embodiments, the method according to the first aspect includes the step of outputting a diagnosis of the subject based on the subject-specific parameters.

In some embodiments, the method according to the first aspect includes the step of outputting a suggested treatment solution or regimen of the subject based on the subject specific parameters.

In some embodiments, the network of interconnected deformable mesh elements form an unstructured mesh.

In some embodiments, the method includes the step of feeding the patient-specific parameters back as inputs to the geometric model and modifying one or more anatomical parameters based on the patient-specific parameters.

In some embodiments, the method includes the step of feeding the patient-specific parameters to a machine learning algorithm to generate revised anatomical parameters and feeding these revised anatomical parameters back as inputs to the geometric model.

In some embodiments, the solid domain includes a region that is fixed in geometric space which corresponds to a posterior part of the upper airway that is attached to a patent's neck.

In some embodiments, the anatomical parameters include a tissue compressibility.

In some embodiments, the anatomical parameters vary depending on a patient's wakefulness state and/or predefined position.

A second aspect of the present invention provides a method of generating a dynamic virtual airway model of a subject, the method including the steps:
  receiving one or more tomographic images of a subject, the image including the subject's upper airway region captured at a predefined breathing state;
  generating, from the one or more tomographic images, a three dimensional geometric model of the upper airway, the geometric model including a network of interconnected deformable mesh elements collectively defining:
    a fluid domain indicative of an interior of the upper airway region through which fluids are able to flow; and
    a solid domain indicative of an exterior of the upper airway region, the solid domain defining a single unitary model of the entire upper airway region segmented into a plurality of predefined geometric regions, each predefined geometric region being defined by one or more anatomical parameters;
  performing a computer simulation on the geometric model to simulate a behaviour of the upper airway region when the subject is positioned in a predefined position, the computer simulation including:
    performing a Computational Fluid Dynamics (CFD) analysis on the fluid domain;
    performing a Fluid-Structure Interaction (FSI) analysis between the fluid and solid domains under the influence of an applied gravity effect at a predefined direction through the geometric model corresponding to the predefined position; and
    outputting a dynamic virtual airway model indicative of the subject's upper airway region.

In some embodiments, the method includes the steps of:
  using a machine learning algorithm to compare the dynamic virtual airway model with real dynamic patient data to generate revised anatomical parameters; and
  feeding the revised anatomical parameters back as inputs to the geometric model to generate a revised dynamic virtual airway model.

A third aspect of the present invention provides a method of simulating behaviour of an upper airway of a subject, the method including the steps:
  i. performing a computer simulation on a three dimensional geometric model of the upper airway to simulate behaviour of the upper airway when the subject is positioned in a predefined position, wherein:
    the geometric model is generated from one or more tomographic images of the subject, the image including the patient's upper airway region captured at a predefined breathing state; and
    the geometric model includes a network of interconnected deformable mesh elements collectively defining:
      a fluid domain indicative of an interior of the upper airway region through which fluids are able to flow; and
      a solid domain indicative of an exterior of the upper airway region, the solid domain defining a single unitary model of the entire upper airway region segmented into a plurality of predefined geometric regions, each predefined geometric region being defined by one or more anatomical parameters;
  ii. performing a Computational Fluid Dynamics (CFD) analysis on the fluid domain;
  iii. performing a Fluid-Structure Interaction (FSI) analysis between the fluid and solid domains under the influence of an applied gravity effect at a predefined direction through the geometric model corresponding to the predefined position; and
  iv. outputting subject-specific parameters indicative of the behaviour of the upper airway.

A fourth aspect of the present invention provides a method of assessing a subject's likelihood of having Obstructive Sleep Apnoea, the method including the steps:
  receiving one or more tomographic images of the subject, the image including the patient's upper airway region captured at a predefined breathing state;
  generating, from the one or more tomographic images, a three dimensional geometric model of the upper airway, the geometric model including a network of interconnected deformable mesh elements collectively defining:
    a fluid domain indicative of an interior of the upper airway region through which fluids are able to flow; and
    a solid domain indicative of an exterior of the upper airway region, the solid domain defining a single unitary model of the entire upper airway region segmented into a plurality of predefined geometric regions, each predefined geometric region being defined by one or more anatomical parameters;

performing a computer simulation on the geometric model to simulate behaviour of the upper airway when the subject is positioned in a predefined position, the computer simulation including:

performing a computational fluid dynamics (CFD) analysis on the fluid domain;

performing a fluid-structure interaction (FSI) analysis between the fluid and solid domains under the influence of an applied gravity effect at a predefined direction through the geometric model corresponding to the predefined position; and outputting subject-specific parameters indicative of the behaviour of the upper airway; and performing an assessment of the subject's likelihood of having Obstructive Sleep Apnoea based on the subject-specific parameters.

A fifth aspect of the present invention provides a method of assessing a subject's response to a treatment regimen for treating Obstructive Sleep Apnoea, the method including the steps:

a) before applying a treatment regimen to the subject:
  i. receiving one or more tomographic images of the subject, the image including the patient's upper airway region captured at a predefined breathing state;
  ii. generating, from the one or more tomographic images, a three dimensional geometric model of the upper airway, the geometric model including a network of interconnected deformable mesh elements collectively defining:
    a fluid domain indicative of an interior of the upper airway region through which fluids are able to flow; and
    a solid domain indicative of an exterior of the upper airway region, the solid domain defining a single unitary model of the entire upper airway region segmented into a plurality of predefined geometric regions, each predefined geometric region being defined by one or more anatomical parameters;
  iii. performing a computer simulation on the geometric model to simulate behaviour of the upper airway when the subject is positioned in a predefined position, the computer simulation including:
    performing a Computational Fluid Dynamics (CFD) analysis on the fluid domain;
    performing a Fluid-Structure Interaction (FSI) analysis between the fluid and solid domains under the influence of an applied gravity effect at a predefined direction through the geometric model corresponding to the predefined position; and
  iv. outputting subject-specific parameters indicative of the behaviour of the upper airway; and
b) applying a treatment regimen to the subject;
c) repeating steps a)i-iv on the subject; and
d) performing an assessment of the subject's response to the treatment regimen by comparing the subject-specific parameters before and after applying a treatment regimen.

A sixth aspect of the present invention provides a method of optimising a treatment regimen of a subject for treating Obstructive Sleep Apnoea, the method including the steps:

a) receiving one or more tomographic images of the subject, the image including the patient's upper airway region captured at a predefined breathing state;
b) generating, from the one or more tomographic images, a three dimensional geometric model of the upper airway, the geometric model including a network of interconnected deformable mesh elements collectively defining:
  a fluid domain indicative of an interior of the upper airway region through which fluids are able to flow; and
  a solid domain indicative of an exterior of the upper airway region, the solid domain defining a single unitary model of the entire upper airway region segmented into a plurality of predefined geometric regions, each predefined geometric region being defined by one or more anatomical parameters;
c) performing a computer simulation on the geometric model to simulate behaviour of the upper airway when the subject is positioned in a predefined position, the computer simulation including:
  performing a Computational Fluid Dynamics (CFD) analysis on the fluid domain;
  performing a Fluid-Structure Interaction (FSI) analysis between the fluid and solid domains under the influence of an applied gravity effect at a predefined direction through the geometric model corresponding to the predefined position; and
d) outputting subject-specific parameters indicative of the behaviour of the upper airway;
e) selectively modifying one or more of the anatomical parameters based on the subject-specific parameters;
f) repeating steps a) to e) until one or more of the subject-specific parameters reach a predefined desired value; and
g) determining a treatment regimen for the patient based on the subject-specific parameters.

A seventh aspect of the present invention provides a computer system configured to implement a method according to any one of the first to fifth aspects.

An eighth aspect of the present invention provides a computer program comprising instructions which, when executed by a computer, cause the computer to carry out the method according to any one of the first to fifth aspects.

A ninth aspect of the present invention provides a computer-readable storage medium comprising instructions which, when executed by a computer, cause the computer to carry out the method according to any one of the first to fifth aspects.

BRIEF DESCRIPTION OF DRAWINGS

Preferred embodiments of the disclosure will now be described, by way of example only, with reference to the accompanying drawings. It will be appreciated that the embodiments shown are examples only and are not to be taken as limiting the scope of the invention as defined in the claims appended hereto.

DETAILED DESCRIPTION

The embodiments disclosed and illustrated herein will be described with reference to observing and measuring breathing performance of the upper airway region of a human. However, it will be appreciated that the disclosure is also applicable to observing and measuring other behaviour of the upper airway region in humans such as swallowing. It will also be appreciated that the disclosure may be applicable to observing and measuring breathing and other behaviour of the upper airway of non-human organisms such as cats, dogs and other animals.

For the purpose of validating the present disclosure, the methodology was performed on a 50 year old male patient having a body mass index (BMI) of 26 and being pre-diagnosed with severe OSA through a PSG study. Results discussed herein will be in reference to this patient.

Figure 1A:
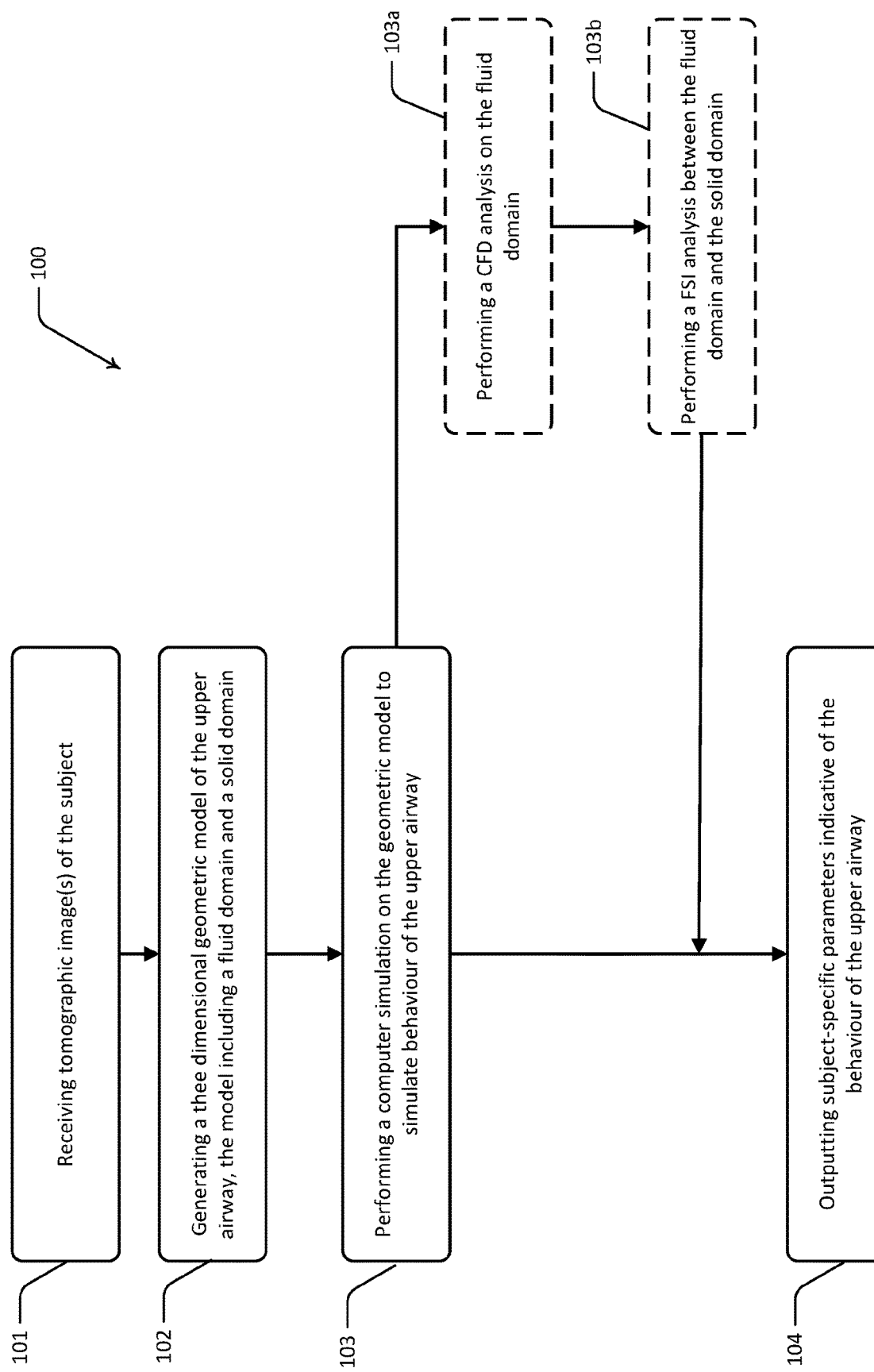
FIG. 1A is a process flow diagram illustrating the primary steps in a method of simulating behaviour of an upper airway of a subject.

Referring initially to FIG. 1A, there is illustrated a method 100 of simulating behaviour of an upper airway of a subject. Method 100 will be described with reference to the system 200 illustrated in FIG. 2, wherein the subject is patient 201.

At step 101 of method 100, one or more tomographic images of the patient 201, are received. The one or more images include the patient's upper airway region and may also include other regions of the patient. For consistency, the images should be captured as fast as possible in a "static" mode at one of a plurality of predefined breathing states which occur during a breathing cycle. Example breathing states include a slightly open mouth state, a relaxed state and a stop breathing state (equivalent to a position at the end of exhaling). To achieve this, the patient is asked to stop breathing, relax and slightly open mouth during CT scanning.

To provide high spatial and depth resolution, the images are preferably Computed Tomography (CT) images obtained from a computed tomography imaging device 203. However, in other embodiments, the CT images may be replaced by magnetic resonance images (MRI) or the like with sufficient spatial and depth resolution. As mentioned below, MRI images and/or magnetic resonance elastography (MRE) images may be used in conjunction with the CT images to augment the model.

The resolution of the images should be sufficient to spatially resolve small features and structures within the upper airway. Preferably, the resolution of the CT images is sub-mm in size. By way of example, a three dimensional CT image may have a spatial resolution of about 0.5-1 mm in the scanning z axis and have a spatial resolution of about 0.5 mm in the x-y (slice) plane. A three dimensional CT image is typically formed of several hundred two dimensional images (slices) extending in the x-y plane and stacked along the z axis. In one embodiment of the present disclosure, the three dimensional CT image is formed of 1,000 two dimensional images separated by 0.5 mm slices.

The three dimensional CT image was formed using the 3DSlicer software available from www.slicer.org and published in Fedorov A et al. 3D *Slicer as an Image Computing Platform for the Quantitative Imaging Network*, Magnetic Resonance Imaging, 2012 November; 30(9):1323-41 PMID: 22770690. However, it will be appreciated that other publicly available or proprietary software packages are available for constructing three dimensional images from collections of two dimensional images.

The CT images are transferred from imaging device 203 to a computer device 205 which may be in network communication with a server 207, where the images may be stored and accessed for subsequent processing. Alternatively, the CT images may be stored on a remote database and accessed by computer device 205 and/or server 207 over a network as needed.

Figure 2:
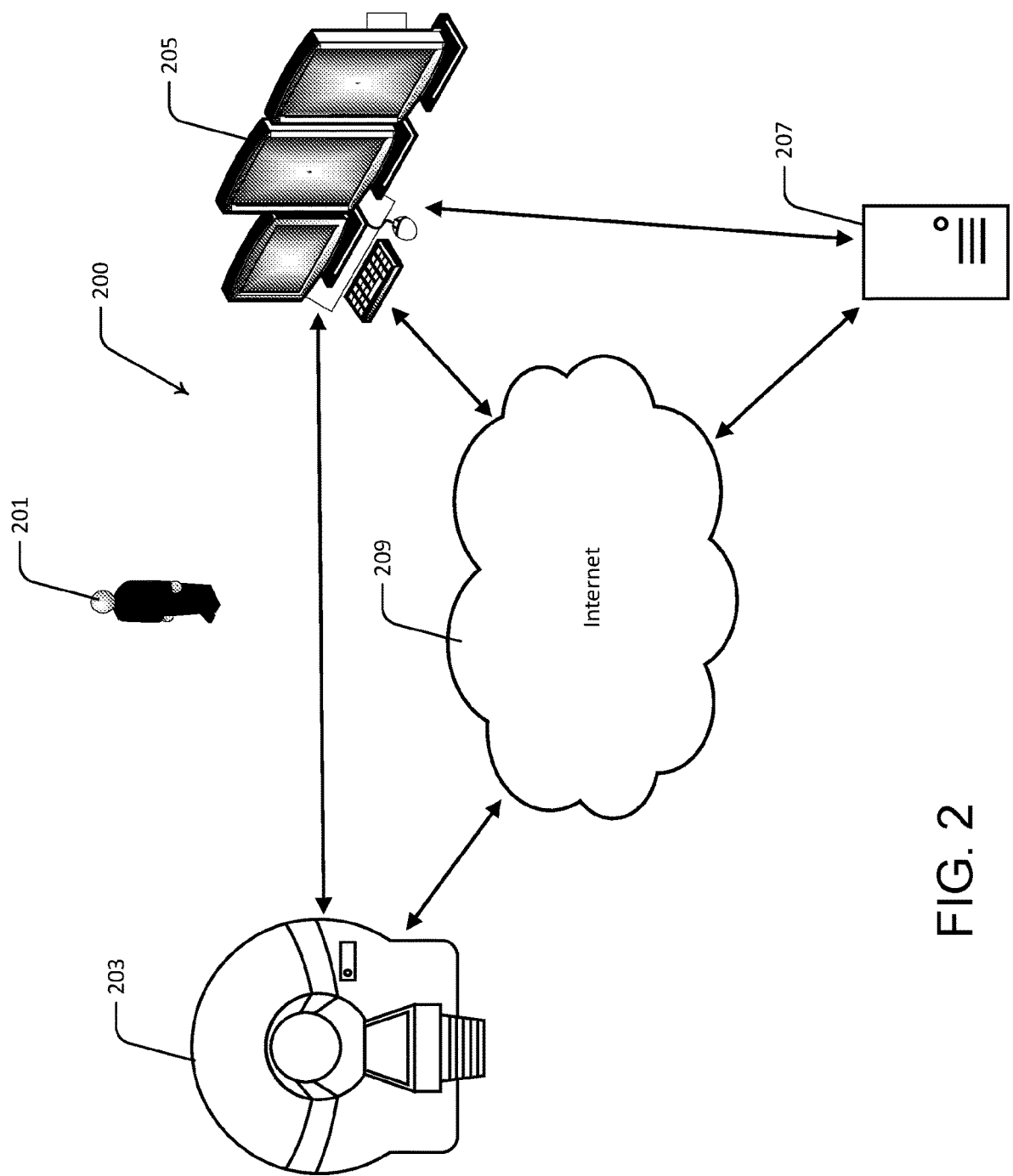
FIG. 2 is a schematic view of an exemplary system configured to implement the method of FIG. 1.

As illustrated in FIG. 2, imaging device 203 may be connected directly to computer device 205, or over a Local Area Network (LAN) such as through a hospital intranet, Ethernet or other internal network. Alternatively, imaging device 203 may communicate with computer device 205 and/or server 207 indirectly over a Wide Area Network (WAN) such as the internet 209. Similarly, computer device 205 may communicate directly with server 207 or indirectly over the internet 209. In some embodiments, suitable computing capability may be incorporated into imaging device 203. In these embodiments, the CT images may be retained locally in imaging device 203 where subsequent processing is performed, such as steps 102 to 104 described below.

Figure 3:
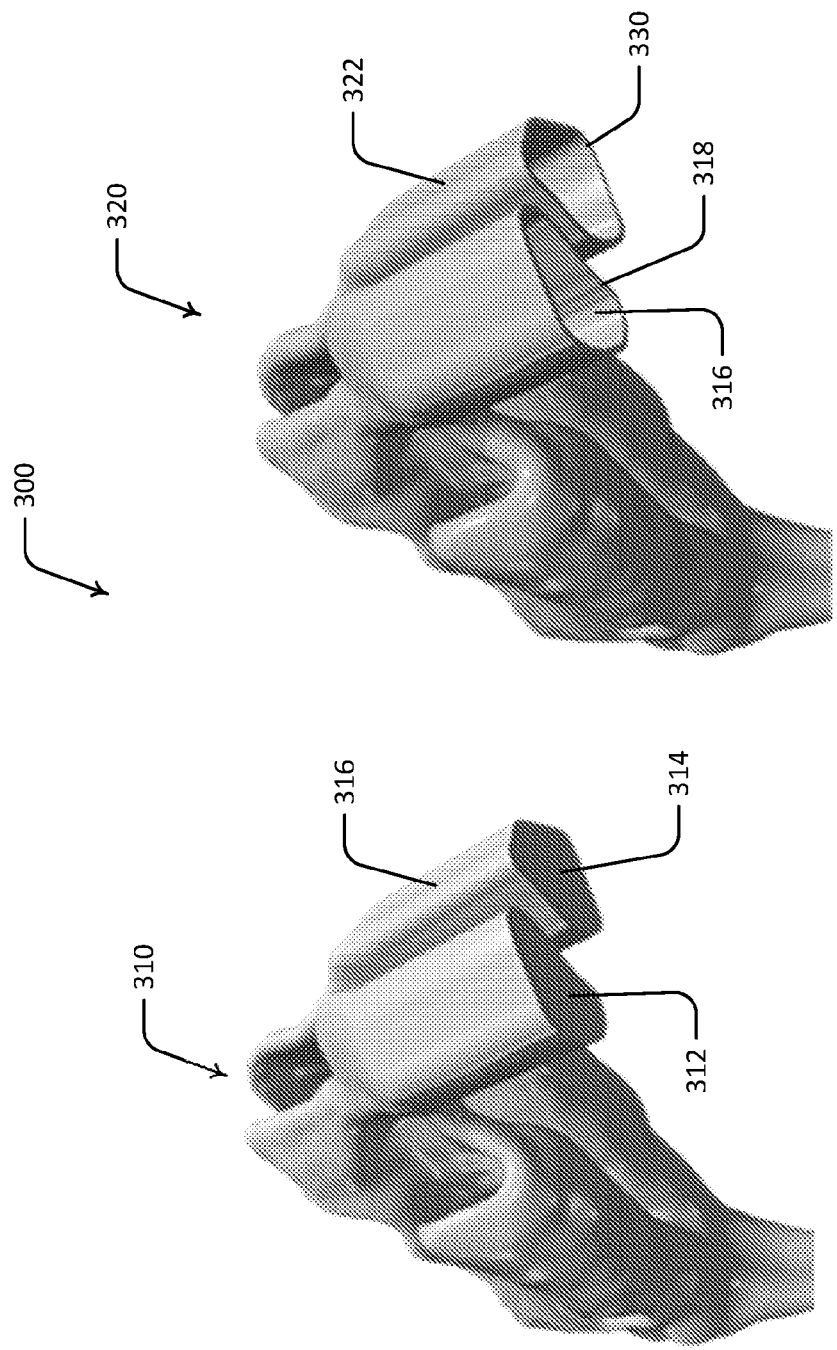
FIG. 3 is a schematic perspective view of a geometric model of an upper airway region, showing both a fluid domain and solid domain.

At step 102, a three dimensional geometric model of the upper airway is generated from the one or more tomographic images using modelling software installed and executed on computer 205. The modelling software may be any suitable software which is able to recognise structural features in the tomographic images, such as via object recognition, edge detection and other techniques that are based on determination of relative intensity values of pixels (or voxels) across the images. By way of example, step 102 may utilise a semi-automated segmentation of CT or MRI images technique, which may implement thresholding or higher order pixel segmentation/classification. An exemplary geometric model 300 is illustrated schematically in FIGS. 3 to 5. The geometric model includes a network of interconnected deformable mesh elements collectively defining two domains: a fluid domain 310 and a solid domain 320, as illustrated in FIG. 3. The fluid domain 310 represents an interior of the upper airway region through which fluids are able to flow. The fluid domain 310 includes a pair of inlets 312 and 314 and walls defining the fluid flow path within the nasal cavities. The solid domain 320 represents the biological tissue that defines the exterior wall of the upper airway region. The solid domain 320 includes solid inner walls 316, fixed faces 318 and 330, and solid outer walls 322 defining the nasal cavities.

Figure 4:
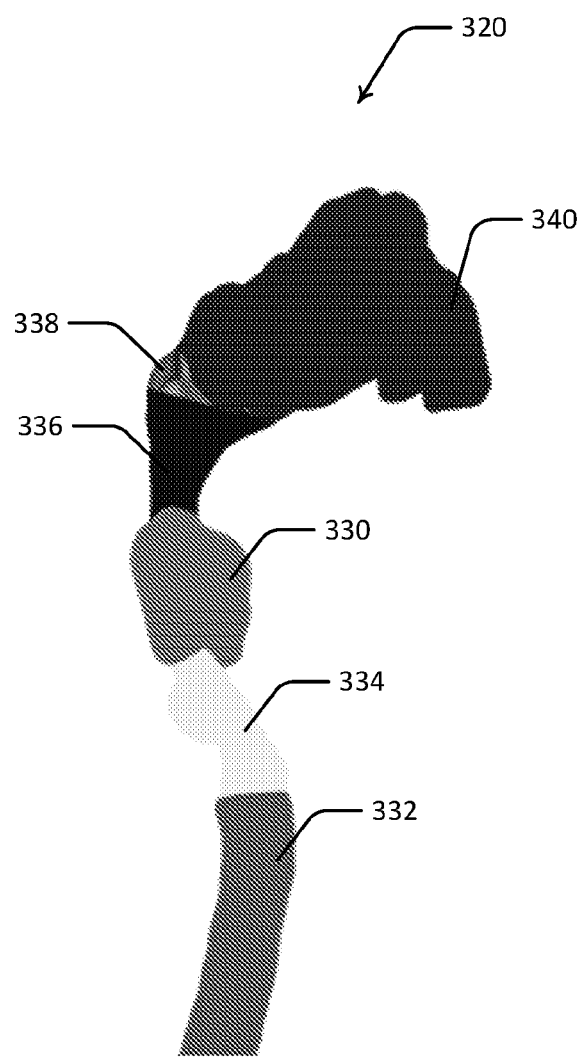
FIG. 4 is a side view of a geometric model of FIG. 3 illustrating different geometric regions representing anatomical regions of the upper airway.

Referring now to FIG. 4, the solid domain 320 is defined so as to include a plurality of predefined geometric regions representing different spatial or anatomical regions of the upper airway. Example geometric regions include a tongue base 330, trachea 332, cricoid cartilage 334, soft palate 336, nasopharynx 338 and nasal cavities 340. In other embodiments, additional regions may be defined such as the epiglottis and pharynx (which, in turn includes the nasal, oro and laryngo regions). In other embodiments, the solid domain 320 may be divided into greater or few geometric regions.

As described below, the different geometric regions representing different anatomical regions are differentiated not only in spatial position within the model but also by various anatomical parameters representing their tissue characteristics. Although the different geometric regions are located separately, they are all included in the solid domain 320 of the model to define a single unitary model that defines the entire upper airway region of the patient. In such a single unitary model, each geometric region is defined by a common set of parameters, including spatial position and anatomical parameters representing tissue characteristics. This provides for more realistic modelling over some prior art methods which model a subset of the regions separately and subsequently combine simulated results from the different models. By way of example, including the nasal cavity region in the single unitary model, the effect of generated vortices due to the nasal cavity (upon inhalation) on the upper airway (specifically pharyngeal region) can be accurately assessed.

Figure 5:
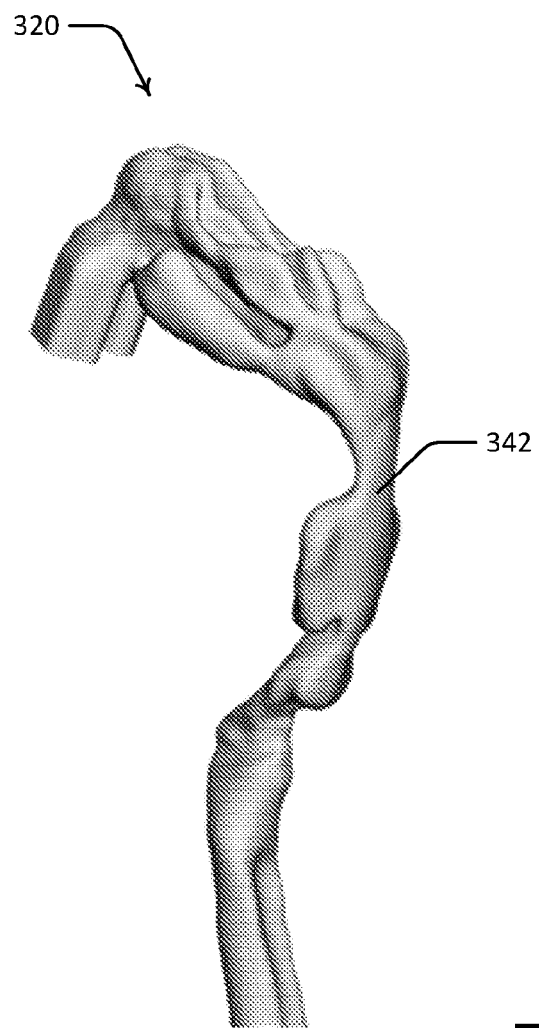
FIG. 5 is a side perspective view of the solid domain illustrated in FIG. 3.

FIG. 5 illustrates an alternative view of the solid domain 320 showing a shaded fixed region 342. This fixed region 342 is fixed in space in the geometric model 300 which is based on the human anatomy where the posterior part of the upper airway from just above the nasopharynx to the oesophagus is attached to the neck.

Due to the complexity of the geometry, an unstructured mesh is used for the geometric model. The unstructured mesh is created using ANSA mesh generation software, developed by BETA CAE Systems, with triangular mesh elements (not shown). To avoid surface shrinkage, a shell smoothing technique is preferably performed. This shell smoothing technique is applied as an extra smoothing step of the top cap of the layers. This allows the growth of more and higher layers of the tissue regions in complex models. Furthermore, to resolve the gradient of velocity fluid flows near the interface between the fluid and solid domains, a finer multi-layer prism mesh is preferably generated near the walls. A final meshing step includes generating a tetrahedral volumetric mesh, which created a maximum skewness of 0.85 with the growth rate of 1.2 to balance the transition between the prism layers and the tetrahedral mesh.

The output of step 102 is a Stereolithography (.STL) file format having the upper airway represented as an unstructured surface of tetrahedral mesh elements (the three dimensional geometric model). As the model is formed as a single unitary model, the .STL file output at step 102 includes each of the predefined geometric regions representing different anatomical regions of the upper airway. It will be appreciated that different meshing software may be used and mesh elements other than triangles may be used to define the mesh geometry. Also, different file formats may be used to digitally represent the geometric model.

Exemplary mesh parameters for three different exemplary meshes (M1, M2 and M3) are outlined in Table 1 below. Here, $N_N$ represents the number of nodes, $N_e$ represents the number of elements, $\Delta T$ represents the time step, h represents a mean edge length of elements, $h_{bl}$ represents a height of the first element in the prism layer $N_{bl}$ represents a number of prism layers and $R_{bl}$ represents the prism growth ratio.

TABLE 1

| Mesh | $N_N(\times 10^6)$ | $N_e(\times 10^6)$ | $\Delta T \times (\mu S)$ | h × (mm) | $h_{bl}(\mu m)$ | $N_{bl}$ | $R_{bl}$ |
|---|---|---|---|---|---|---|---|
| M1 | 1.2 | 4 | 1000 | 0.3 | 0.015 | 9 | 1.2 |
| M2 | 1.7 | 5 | 100 | 0.15 | 0.0021 | 15 | 1.2 |
| M3 | 2.4 | 7.6 | 100 | 0.10 | 0.00038 | 20 | 1.2 |

Each predefined geometric region is defined at least in part by one or more anatomical parameters including tissue structural properties, as measured by a tissue's Young modulus, tissue density, Poisson's Ratio, tissue compressibility, and shape and size of a geometric region. These parameters may be input based on data reported in the literature and/or may be patient-specific data. By way of example, tissue stiffness parameters such as Young modulus may be obtained from MRE images of the patient. Data from patients of similar age, gender or ethnicity may also be used as inputs.

The solid and fluid domains are interactive in the sense that the size, shape and deformability of the geometric regions define the fluid domain. Likewise, the forces resulting from the fluid flow through the fluid domain impart structural changes on the solid domain. In this regard, geometric regions facilitate both the passage of fluid (e.g. in the trachea where tissue stiffness is important) and the obstruction of fluid (e.g. in the tongue region where shape and size are more important parameters).

Example anatomical parameters used in this disclosure are illustrated in Table 2 below. However, it will be appreciated that these parameters may vary with age, sex and race of the patient, as well as the state of the patient such as awake, half-awake or deep sleep states. By way of example, during sleep, the upper airway muscles are more relaxed compared to awake. Thus, upper airway muscle are softer during sleep and harder when awake. This can be included in the present model by designating certain geometric regions, particularly the tongue base, with higher values of Young modulus (increased stiffness) and lower values of Poisson's Ratio during wakeful states than a sleep state. These parameters, particularly the tissue stiffness measured by the Young modulus, may also vary with the position in which the patient is laying/seated.

TABLE 2

| Anatomical region | Mean Young modulus (MPa) | Density (kg/m$^3$) | Poisson's Ratio |
|---|---|---|---|
| Trachea | 4.128 | 1,250 | 0.30 |
| Cricoid | 2.534 | 1,250 | 0.30 |
| Nasopharynx | 1.764 | 1,060 | 0.30 |
| Tongue base | 1.416 | 1,100 | 0.49 |
| Soft palate | 0.99 | 1,000 | 0.49 |
| Nasal cavities | 2.02e$^6$ | 1,000 | 0.30 |

In some embodiments, steps 101 and 102 may be performed by a third party as pre-processing steps. In these embodiments, the pre-processed geometric model of a patient can be supplied to a clinician or other party for subsequent analysis.

Once the geometric model is generated, at step 103, a computer simulation is performed on the geometric model to simulate a breathing cycle to predict behaviour of the upper airway when the patient 201 is positioned in a predefined position. Example predefined positions include a prone laying position, a supine laying position, a lateral left laying position, a lateral right laying position and a seated position. However, it will be appreciated that the present invention provides capability for simulating any patient position or orientation. When used as an input, the position of the patient varies parameters such as Poisson's Ratio, tissue region size and region shape for certain regions and defines a direction of gravity, which also effects the performance of the simulation as described below. Mathematically, this variability of anatomical parameters with patient position// orientation or wakefulness state will change the predicted results of airway deformation.

In addition to the geometric model and patient position, other inputs to the simulation include cyclic function parameters. In the present implementation, the cyclic function was defined in the lower part of the trachea, which is where the cyclic function parameters are set. It will be appreciated that cyclic function parameters may be set at different locations and/or at multiple locations within the upper airway region. Example cyclic function parameters include:

Flow rate. In one embodiment, this parameter was set to 10 L/min.
Peak flow velocity. In one embodiment, this parameter was set to 0.8 m/s.
Breathing frequency. In one embodiment, this parameter was set to 0.25 Hz.

Example computer simulation software used for step 103 includes the "Alya" High Performance Computational Mechanics software managed and run by the Barcelona Supercomputing Centre in Barcelona, Spain.

The computer simulation includes, at sub-step 103a, performing a CFD analysis on the fluid domain 310. This sub-step models the fluid flows through the upper airway region during behaviour such as breathing by the patient 201.

At sub-step 103b, an FSI analysis between the fluid domain 310 and solid domain 320 is performed under the influence of an applied gravity effect at a predefined direction through the geometric model corresponding to the predefined position. This sub-step models the structural deformation of the anatomical regions of the upper airway during the behaviour such as breathing by the patient 201. Sub-step 103b can be performed by applying a pressure on the tongue base. The pressure is calculated using the mass of the patient's tongue (input as the mass parameter) and applying a gravitational acceleration vector at a direction corresponding to the predefined position. By way of example, when the patient is lying in the supine position, the gravitational acceleration vector is applied vertically downward across the upper airway region (from left to right in FIG. 5).

Sub-steps 103a and 103b are simulated in conjunction with one another as a coupled simulation as the fluid flow causes structural deformation which, in turn, alters the fluid domain shape and fluid dynamics, as described above. This coupled processing is illustrated schematically in FIG. 1B.

The deformability of the geometric model during simulation is facilitated by the tissue parameters (i.e. Young's modulus and Poisson's ratio) in conjunction with the flexible mesh structure used to define the different geometric regions. As such, each geometric region of the solid domain can be set to have different levels of deformity. An unstructured mesh is used in the preferred embodiments of the present invention as it is more efficient when dealing with complex geometry (e.g. the nasal cavity).

Figure 1B:
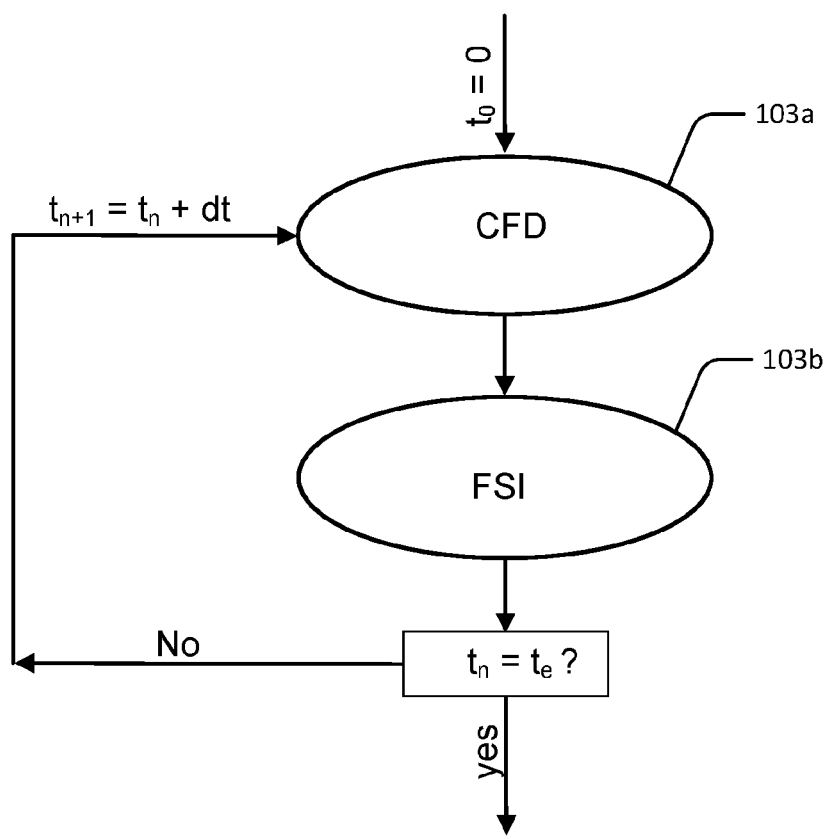
FIG. 1B describes an exemplary iteration process used in performing the CFD and FSI steps of the computation.

Sub-steps 103a and 103b are performed iteratively as illustrated in FIG. 1B. In this iterative process, $t_e$ represents the total/breathing cycle time (inhale and exhale), $t_0=0$ is the time at the start of the process, $t_n$ is the time at iteration step n and dt is the time increment between iteration steps. In a preferred embodiment CFD is followed by FSI a few one hundredths of a second apart.

Two possible simulation approaches to simulate such a coupled system include a monolithic approach and a staggered/partition approach. The implementation described below relates to a partitioned approach, which typically requires significantly less coding than the monolithic approach.

The mathematical framework behind the computer simulation is set out in detail below.

Finally, at step 104, subject-specific parameters and optionally other information are outputted from the computer simulation. The subject-specific parameters are indicative of the behaviour of the upper airway and may include one or more of:

An apnoea-hypopnea index (AHI) for the patient.
A peak volume flow rate of patient breathing.
An average breathing rate of the patient.
A measure of upper airway closure, deformation or displacement for the patient.
Collapse or partial collapse time of the airway passage during the breathing cycle.
Parameters indicative of airflow and/or displacement of airway walls at any point along the airway and at any point of time during a breathing cycle.

The output patient specific parameters may be finite numbers, ranges or numbers or both. In some embodiments, the patient specific parameters may be qualitative descriptors. Based on these parameters, a clinician is able to provide a diagnosis of the patient, assess the patient's likelihood of having a sleep disorder such as OSA, suggest possible treatment solutions, gauge the efficacy of current treatment regimens, determine an optimised treatment regimen and/or suggest changes to current treatment regimens. In the case of gauging efficacy, the above method could be performed before and after a treatment regimen is implemented and the patient-specific parameters compared.

In the case of determining an optimised treatment regimen, the above method could be performed iteratively with patient-specific parameters fed back as inputs to modify one or more anatomical parameters. By iteratively performing this feedback process, appropriate anatomical parameters can be determined which optimise the patient-specific parameters. These anatomical parameters can be used to determine a suitable treatment regimen which achieves these optimised patient-specific parameters.

In some embodiments, this iterative process may involve artificial intelligence such as machine learning systems to assist with this assessment/analysis process. This is described in more detail below.

By way of example, possible treatments to a patient may include one or more of:

Surgery of the nose, tonsils, jaw and/or roof of the mouth.
Application of a passive medical device such as mandibular advancement device. Suitable devices may include the "$O_2$Vent" device developed by Oventus Medical Limited, or those described in PCT Patent Application Publications WO2018068085 or WO2015149127, for which Oventus Medical Limited is the applicant.

Application of an active medical device or a positive pressure device such as CPAP or a range of other devices that work to change air flow patterns.

In addition to the above parameters, in some embodiments a graphical representation of a simulated breathing cycle of the patient may be outputted from the computer simulation. The graphical representation may be in the form of still images captured at predetermined times during the simulation, a video sequence of images illustrating the breathing process dynamically or other data represented graphically. One example of a graphical representation includes a dynamic virtual airway model of the patient. This may represent behaviour other than breathing, such as swallowing.

Example graphical representations output from the computer simulation are illustrated in FIGS. 6 to 12. Some of these are discussed below.

A dynamic virtual airway model of the patient may be compared with real dynamic data such as a video sequence obtained from MRI images for assessment of accuracy and for correcting anatomical parameters such as tissue properties. In some embodiments, computer device 205 or another network connected processor hosts a machine learning algorithm that receives MRI images or other images of the patient as training data to refine the model such that the dynamic virtual airway model more closely matches the real data. The machine learning algorithm may be supervised or unsupervised and based on observations of parameters like a degree of deformation of the airway. In some embodiments, the machine learning algorithm may employ image processing techniques such as object recognition and edge detection to compare spatial dimensions of the upper airway region in the dynamic virtual airway model and MRI images throughout a breathing cycle. In one embodiment, the machine learning may be a rule-based algorithm that learns relationships between parameters such as Young modulus, density and Poisson's Ratio to improve the accuracy of the model.

Thus, the addition of MRI data can be used to augment the model. A similar process may be adopted using a video sequence of CT images. Using such a machine learning technique, the need for subjecting the patient to an X-ray process to obtain high resolution CT images may be avoided. By using an input MRI image or placeholder input parameters indicative of a patient, the model may be iteratively updated based on machine learning until the parameters closely match that of the patient and the dynamic virtual airway model accurately models the patient.

The computer simulation may also output a diagnosis of the subject based on the subject-specific parameters. Example diagnoses include a risk of having/developing OSA, a designation that the patient suffers from OSA and to what degree based on the AHI measurement. Such outputs could include parameters, a range of parameters, quantified output, qualitative/descriptive (e.g. high/low) or a combination thereof.

The computer simulation may also output a suggested treatment solution or regimen of the patient based on the subject specific parameters. In some embodiments, the computer simulation may provide an intervention output based on intervention inputs, simulating behaviour of the upper airway with interventions such as a mandibular splint or surgery. In some embodiments, Continuous Positive Airway Pressure (CPAP) or other therapies may be simulated.

Mathematical Framework of the Computer Simulation

The Alya simulation code solves the Navier-Stokes equations which govern fluid motion in the fluid domain. The following are the Navier-Stokes equations for an incompressible fluid:

$$\rho_f \frac{\partial u_f}{\partial L} + \rho_f (u_f \cdot \nabla) u_f - \nabla \cdot [2\mu_f \epsilon(u_f)] + \nabla_p = \rho f \quad (1)$$

$$\nabla \cdot u_f = 0 \quad (2)$$

Where, $u_f$ is the fluid velocity field, and viscosity of the fluid defined as $\mu_f$. Accordingly, the $\rho_f$ and p are the density and pressure of the fluid respectively and epsilon $\epsilon = \frac{1}{2}(\nabla u_f + \nabla u_f^t)$, is the rate of strain tensor expressed in terms of velocity gradient.

To solve the coupled problem of the fluid and solid domains, definition of appropriate boundary conditions is essential. The boundary condition for the solid domain is as follows:

$$\rho_s \frac{\partial d_s}{\partial t} = \nabla \cdot P + b \quad (3)$$

Where the solid density and solid displacement field defined as $\rho_s$ and $d_s$ respectively. P represents the Piola-Kirchhoff stress tensor and the body force is represented as b.

To meet the requirement for the coupling conditions at the interface, the continuity of the forces and displacements need to be imposed in the continuum level as follows:

$$d_f = d_s \quad (4)$$

$$t_f = -t_s \quad (5)$$

$$u_f = \frac{\partial d_f}{\partial t} \quad (6)$$

Where the deformed solid interface inside the fluid is called $d_f$. The tractions that are exerted on the interface are defined by $t_f$ and $t_s$ for the fluid and solid respectively.

It is also possible to track the solid-fluid interface between the solid and fluid domains of the geometric model as it varies dynamically in the computer simulation. The Arbitrary Lagrangian-Eulerian (ALE) framework is one possible method to follow the interface by translating the fluid equations in a moving Eulerian reference system to the displaced grid that monitors the interface in the mathematical formulation. Example use of this framework is explained broadly C. Farhat and M. Lesoinne and P. Le Tallec, 1998; Perić, 2006; Tayfun E. Tezduyar, 2007. For the moving Eulerian domain, the fluid conservation laws are implemented, and this reference is used to implement the governing equations.

The result of the fluid conservation laws is as follow:

$$\rho_f \frac{\partial u_f}{\partial t} + \rho_f [(u_f - u_m) \cdot \nabla] u_f - \nabla \cdot [2\mu_f \epsilon(u_f)] + \nabla_p = \rho_f f \quad (7)$$

$$\nabla \cdot u_f = 0 \quad (8)$$

Where the velocity domain, which is obtained from the deformed solid domain ($d_m$), is defined as $u_m \cdot d_m$ is obtained from the diffusion equation as follows:

$$\nabla \cdot [c_m \nabla d_m] = 0 \quad (9)$$

Where, in this equation, $c_m$ is the diffusion coefficient term and $d_m$ is the node displacement at the discrete level. $c_m$ is computed to control the stiffness level of the elements and is obtained from the following equation:

$$c_m = AR/V \quad (10)$$

V is the volume of the element and, the aspect ratio is introduced as AR. Where the smaller the element the stiffer they will be, the same story is applicable for the element with larger aspect ratio. Practically, it is found to be useful in terms of preserving the boundary layer elements.

For better understanding of the discretization scheme an algebraic matrix form is used to illustrate the full problem. In the coupling strategy there are three matrices; mesh movement, fluid flow and the solid mechanics problem. Three decoupled system at time $t^{n+1}$ are as follow:

$$A_f u_f = b_f, A_m d_m = b_m, A_s d_s = b_s \quad (11\text{-}13)$$

Where matrices of the fluid flow, mesh displacement and solid mechanics are presented as $A_f$, $A_m$, and $A_s$ respectively. The fluid velocity $u_f$, and the mesh movement determined with respect to the previous time step, which is defined as $d_m$, thus, the solid displacement $d_s$ is calculated based on the original configuration. For instance, if the solid and fluid domains are coincided on the interface or "wet surface", and the nodes on this interface define as the "wet nodes" and any other nodes considered as the "dry nodes", by renumbering the nodes, the wet and the dry nodes can be separated as follows:

$$\begin{pmatrix} A_{ff} & A_{f\Gamma f} & 0 & 0 & 0 & 0 \\ A_{\Gamma ff} & A_{\Gamma f\Gamma f} & 0 & 0 & 0 & 0 \\ 0 & 0 & A_{mm} & A_{m\Gamma m} & 0 & 0 \\ 0 & 0 & A_{\Gamma mm} & A_{\Gamma m\Gamma m} & 0 & 0 \\ 0 & 0 & 0 & 0 & A_{ss} & A_{s\Gamma s} \\ 0 & 0 & 0 & 0 & A_{\Gamma ss} & A_{\Gamma s\Gamma s} \end{pmatrix} \times \begin{pmatrix} u_f \\ u_{\Gamma f} \\ d_m \\ d_{\Gamma m} \\ d_s \\ d_{\Gamma s} \end{pmatrix} = \begin{pmatrix} b_f \\ b_{\Gamma f} \\ b_m \\ b_{\Gamma m} \\ b_s \\ b_{\Gamma s} \end{pmatrix} \quad (14)$$

Where dry nodes defined as the $A_{ii}$ and denoted by $u_i$, also, corresponding matrix to the wet nodes $u_{\Gamma i}$ is $A\Gamma_i\Gamma_i$, alternatively, $A_{i\Gamma_i}$ and $A_{\Gamma_i i}$ represent dry and wet nodes. In the coupling condition the displacement for the fluid mesh and the solid are the same at the wet interface therefore, $$d_{\Gamma m} = d_{\Gamma s} - d_{\Gamma s}(t_n), \quad (15)$$

$d_{\Gamma_s}$ here represents the solid displacement in the previous time step on the wet surface. Note, the fluid velocity of the surface is a dependent of the condition of the wet surface, so if the condition for this surface is non-slipping surface, the fluid velocity at this point will be equal to the velocity of this surface. Alternatively, it can be written:

$$u_{\Gamma f} = \frac{d_{\Gamma m}}{\delta t}. \quad (16)$$

the applied force from fluid to the solid is given by the residual of the momentum equation at the wet surface (Cajas et al., 2018)

$$r_{\Gamma f} = b_{\Gamma f} - A_{\Gamma f f} u_f - A_{\Gamma f\Gamma f} u_{\Gamma f} \quad (17)$$

and must be added to the wet nodes of the solid case if both units of the solid and the fluid equations are the same. Finally, the coupled case is defined as follows:

$$\begin{pmatrix} A_{ff} & A_{f\Gamma f} & 0 & 0 & 0 & 0 \\ 0 & I & 0 & -\frac{I}{\delta t} & 0 & 0 \\ 0 & 0 & A_{mm} & A_{m\Gamma m} & 0 & 0 \\ 0 & 0 & 0 & I & 0 & -I \\ 0 & 0 & 0 & 0 & A_{ss} & A_{s\Gamma s} \\ A_{\Gamma ff} & A_{\Gamma f\Gamma f} & 0 & 0 & A_{\Gamma s s} & A_{\Gamma s\Gamma s} \end{pmatrix} \times \begin{pmatrix} u_f \\ u_{\Gamma f} \\ d_m \\ d_{\Gamma m} \\ d_s \\ d_{\Gamma s} \end{pmatrix} = \begin{pmatrix} b_f \\ 0 \\ b_m \\ -d_{\Gamma s}(t_n) \\ b_s \\ b_{\Gamma f} + b_{\Gamma s} \end{pmatrix} \quad (18)$$

To meet the correct boundary conditions for the mesh movement problem, the $A_{\Gamma_m m} = 0$ and $A_{\Gamma_m \Gamma_m} = I$ matrices are changed. It is significant that the $A_{\Gamma_i \Gamma_i}$, $A_{i\Gamma_i}$, and $A_{\Gamma_i i}$ are normally the function of $u_i$. In addition, the value of these quantities can be used for the problem linearization by implementing the earlier iterations and while defining the coupling strategy. Moreover, $A_{ff}$ and $A_f \Gamma_f$ matrices are defining the coupling of the mesh displacement with the fluid through the mesh velocity which is computed as $d_m/\delta t$ and $d_{\Gamma_m}/\delta t$.

Example Simulation

For the fluid domain 310, four wall boundary conditions are defined; outer and inner walls are defined to be free, and the upper and lower faces are defined to be fixed. A boundary condition of flow rate is set such that the flow rate equals 1.18 L/sec at the bottom of the trachea. This value is based on the measured flow rate from an experimental setup.

For the solid domain 320, only one wall is defined to be fixed, as illustrated by the shaded region 342 in FIG. 5. This is based on the human anatomy where the posterior part of the upper airway from just above the nasopharynx to the oesophagus is attached to the neck.

With the static pressure defined to be equal to the ambient pressure, the flow simulations with a cyclic/sinusoidal form are performed for three scenarios based on different anatomical parameters defined for the tongue base 330 and soft palate 336.

The first scenario is a "soft" scenario in which values for the Young's modulus and Poisson's ratio are in a lowest range based on results in the literature. A "hard" scenario defined Young's modulus and Poisson's parameters based on the highest values of the material properties found in the literature. Finally, a "medium" scenario was defined based on average values of the soft and hard scenarios. Additionally, for each scenario, the density for each region was defined based on values from the literature to account for the effect of gravitational force on the most collapsible regions. The following table illustrates the combination of these three case studies.

TABLE 3

| | Hard scenario | |
|---|---|---|
| Variable Tissues | Young modulus (Pa) | Poisson's ratio |
| Soft palate | 41200 | 0.49 |
| Tongue | 59610 | 0.49 |

TABLE 4

Medium scenario

| Variable Tissues | Young modulus (Pa) | Poisson's ratio |
|---|---|---|
| Soft palate | 31200 | 0.49 |
| Tongue | 39610 | 0.49 |

TABLE 5

Soft scenario

| Variable Tissues | Young modulus (Pa) | Poisson's ratio |
|---|---|---|
| Soft palate | 21200 | 0.49 |
| Tongue | 29610 | 0.49 |

To replicate the breathing function, the following cyclic function parameters were used: Flow rate—15 L/min; Peak velocity—0.84 m/s; Breathing frequency—0.25 Hz. However, it will be appreciated that other values may be used to suit different patients (or subjects in the case of non-humans).

To test the above described methodology, the simulation was performed on a patient in two different sleeping positions: supine and prone. A supine position corresponds to a patient lying on his/her back with the face and torso facing upwards. A prone position corresponds to a patient lying face down. The patient details and parameters are as described above.

When the patient is sleeping in the supine position, gravitational acceleration is imposed as a vector on the negative Y axis. To observe the effect of the gravity on soft tissues, the muscles that support the tongue against the gravity are assumed to be fully relaxed, i.e. no muscular forces applied on tongue except for gravitational.

For the simulation, the density of the various geometric regions of the upper airway was set to those defined in Table 2.

Example results from the simulation are illustrated in FIGS. 6-12.

Figure 6:
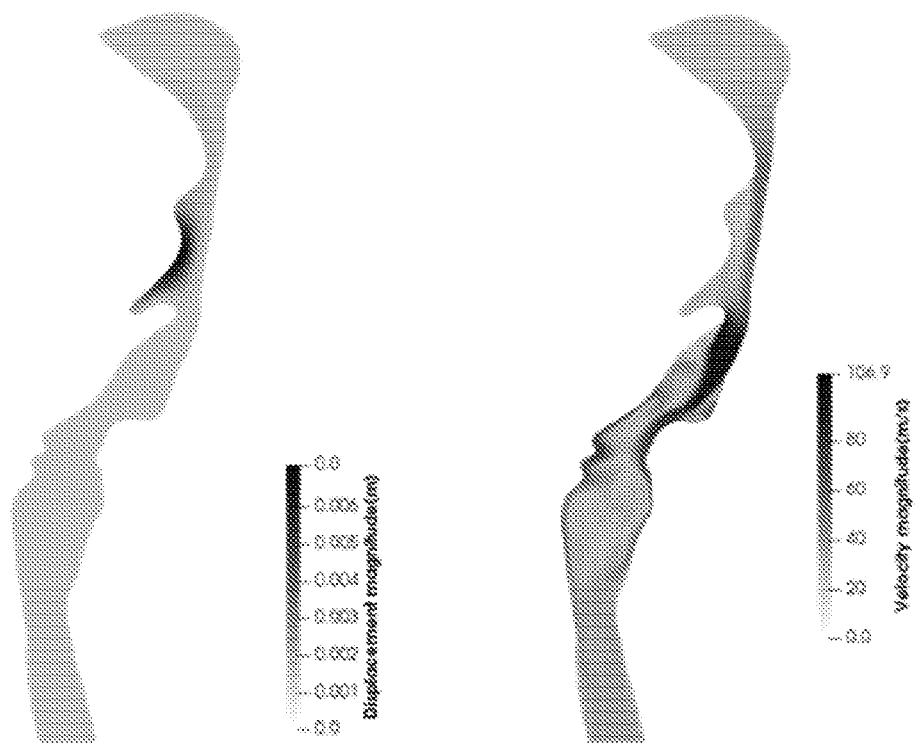
FIG. 6 illustrates cross-section views of the upper airway fluid and solid domains.

FIG. 6 illustrates cross-section views of the upper airway fluid and solid domains. The left image shows the displacement magnitude and the right image shows the velocity magnitude for the deformed model.

Figure 7:
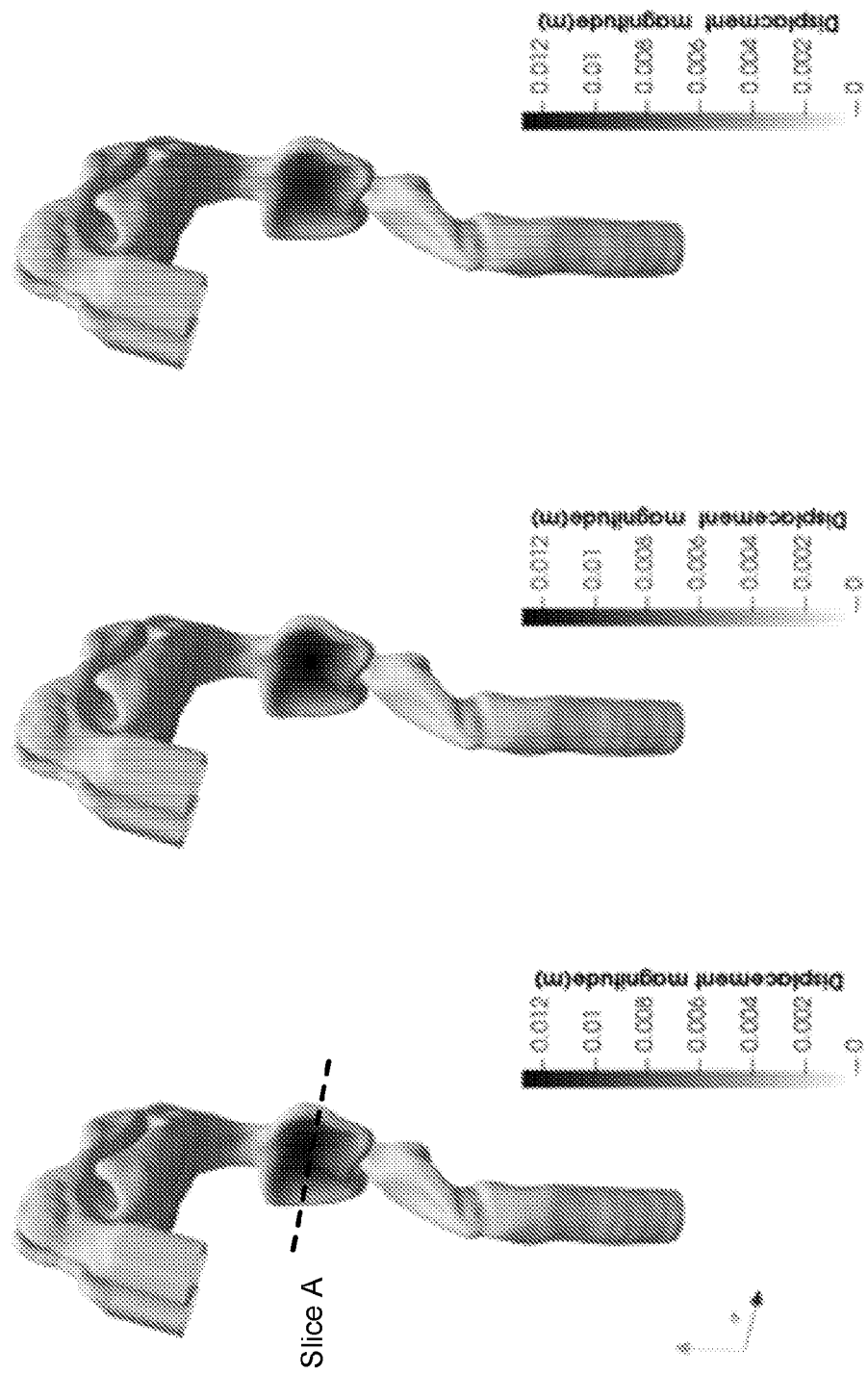
FIG. 7 illustrates displacement comparison between three different stiffness cases with various material properties with gravitational force imposed in the Y axis.

FIG. 7 illustrates displacement comparison between three different stiffness cases with various material properties with gravitational force imposed in the Y axis. Images from left to right respectively are "Soft", "Medium" and "Hard" case studies.

Figure 8:
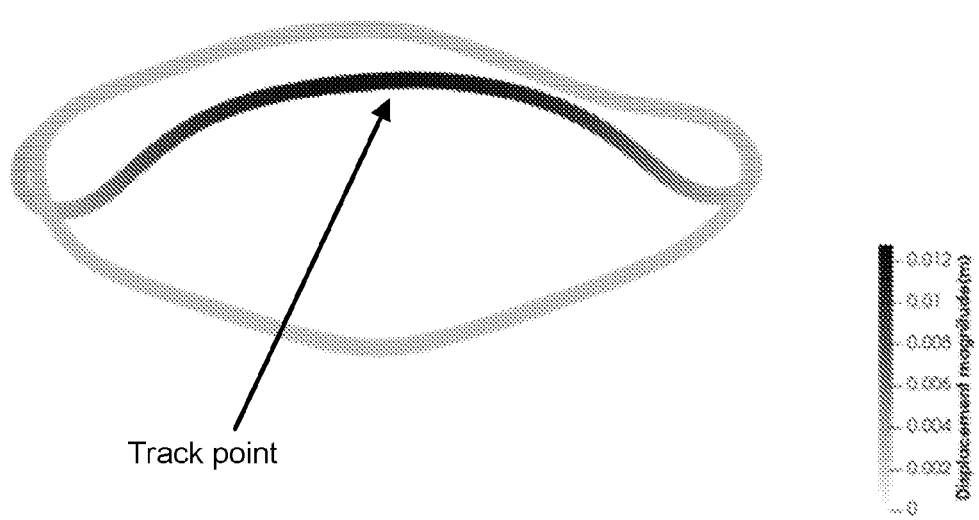
FIG. 8 illustrates slice A from the tongue-base region (see FIG. 7) with a track point located in the maximum area of deflection tracked the deformation magnitude for three different case studies 'Soft', Medium and Hard"

FIG. 8 illustrates slice A from the tongue-base region (see FIG. 7) with a track point located in the maximum area of deflection tracked the deformation magnitude for three different case studies "Soft, Medium and Hard". The grey surrounding line shows the tongue base area before deformation and the central dark region is the maximum deflection area that caused during the inhalation.

Figure 9:
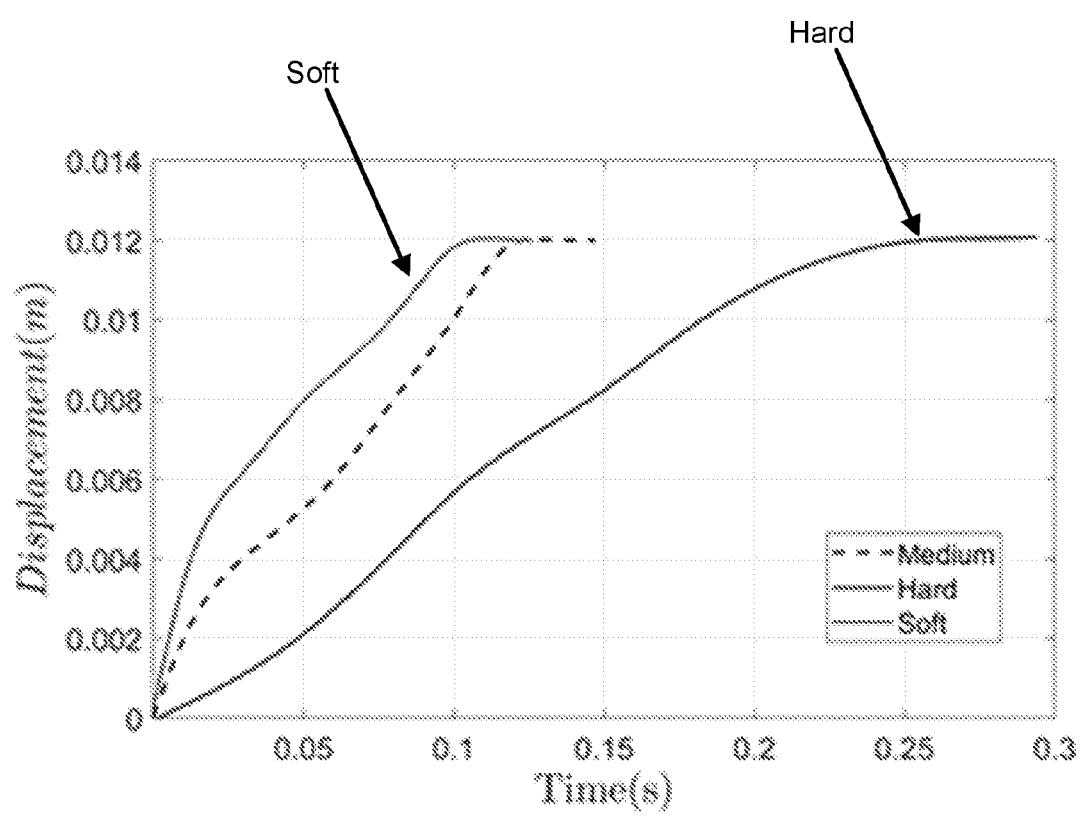
FIG. 9 illustrates a deflection magnitude in three different stiffness case studies.

FIG. 9 illustrates a deflection magnitude in three different stiffness case studies. The topmost solid line represents the soft material properties that collapsed after 0.115 s. From this graph, it can be seen that the collapse time for medium stiffness (0.14 s) and hard (0.28 s) material properties is longer due to the material stiffness.

Figure 10:
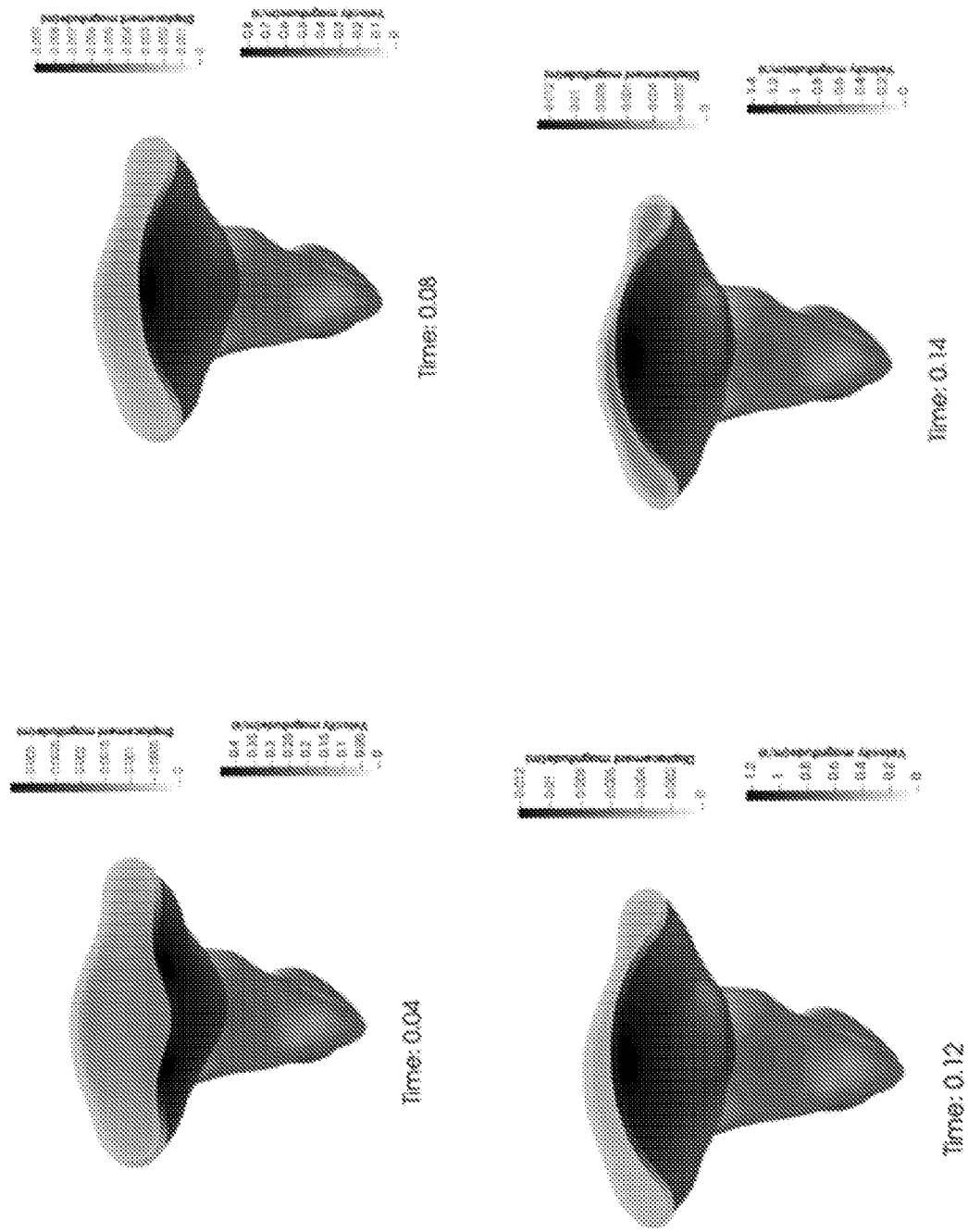
FIG. 10 illustrates the effect of gravitational acceleration in the supine sleeping position for the 'Medium' stiffness case study.

FIG. 10 illustrates the effect of gravitational acceleration in the supine sleeping position for the "Medium" stiffness case study. The cross section in the Z direction in the tongue base shows the displacement comparison during different time steps.

Figure 11:
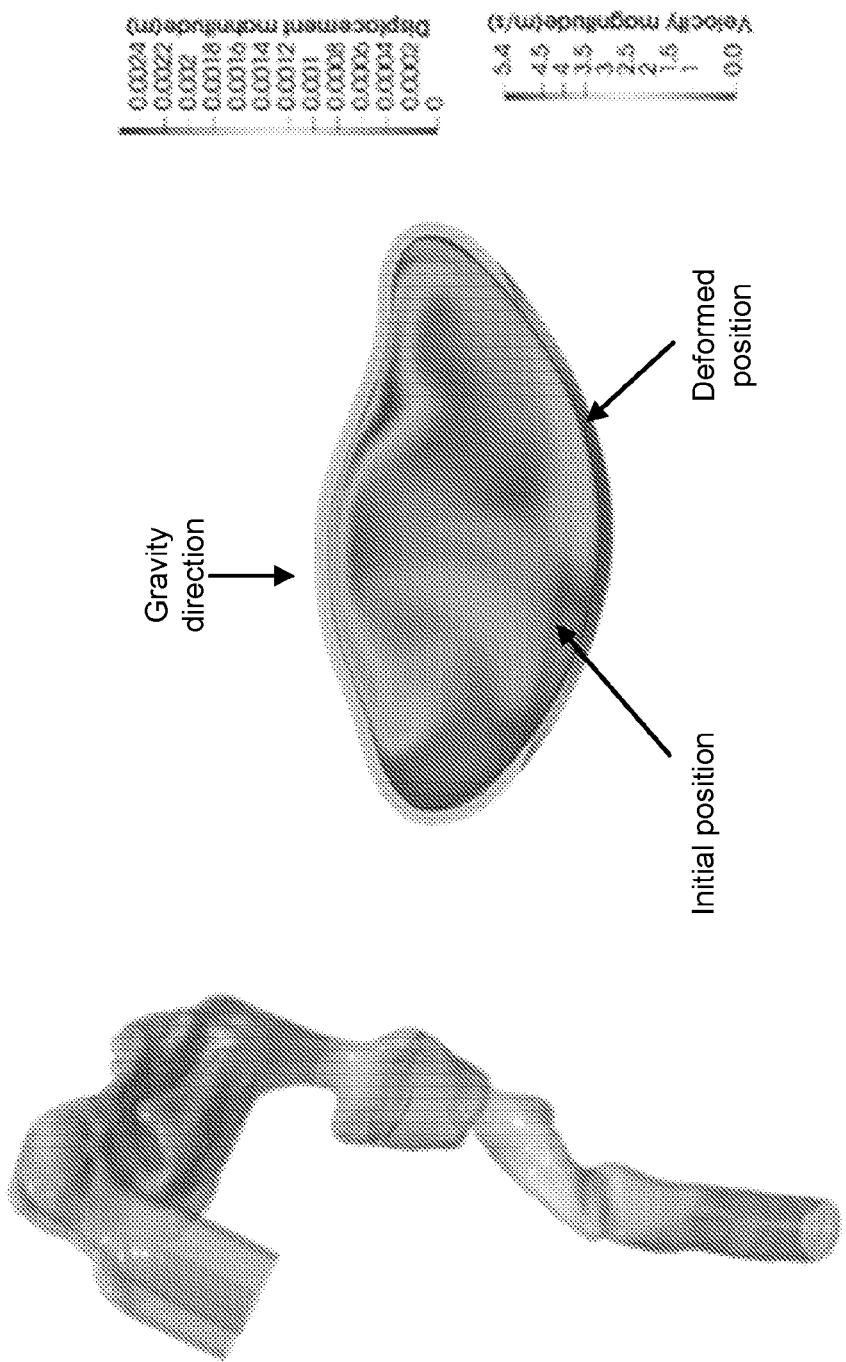
FIG. 11 illustrates deformation magnitude in the prone sleeping position for 1.0 s after inhalation.

FIG. 11 illustrates deformation magnitude in the prone sleeping position for 1.0 s after inhalation. Here, gravity force is imposed downward in the Y direction.

Figure 12:
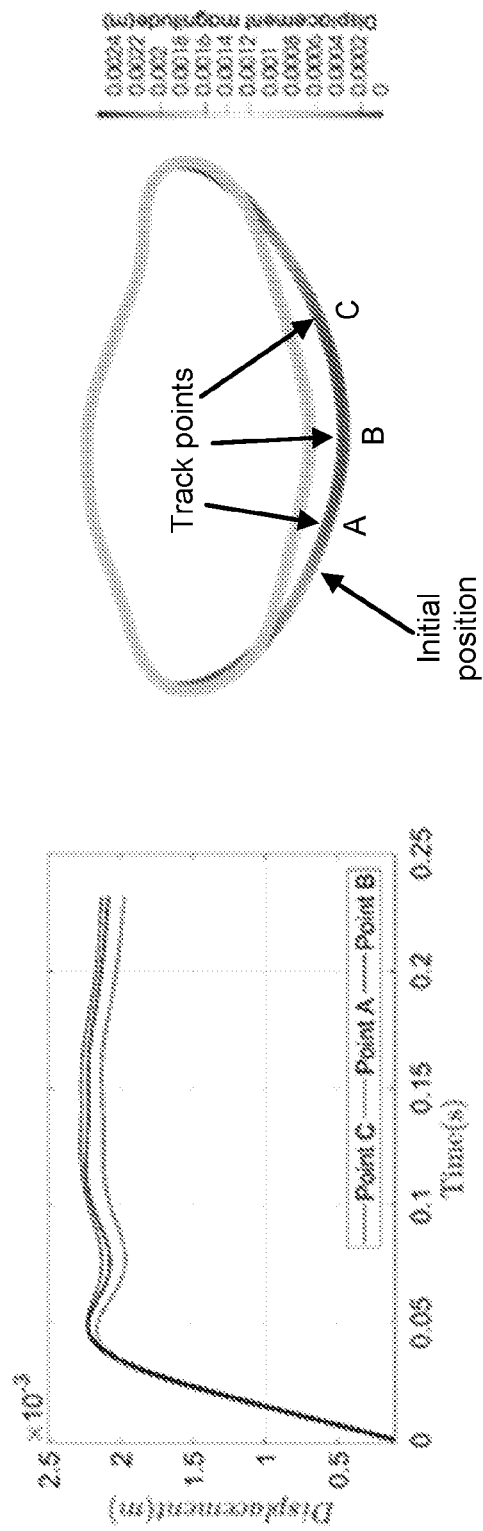
FIG. 12 illustrates deformation in three different locations in the tongue base cross-section area, for the 'Medium' stiffness case model.

FIG. 12 illustrates deformation in three different locations in the tongue base cross-section area, for the "Medium" stiffness case model.

Results from the numerical model shows the maximum deformation in the tongue base region with an average of 5.6 mm of displacement.

Example Applications

The above methodology has applications in simulating upper airway behaviour in a virtual patient. This has utility as an investigative tool for testing new therapies in a safe and cost effective manner.

The above methodology is able to be used as a screening tool to refer patients to specialists or for a sleep study. The methodology may also be used as a personalised treatment planning tool. For example, the patient-specific simulation may be utilised to evaluate the patient's response to intervention or current treatment regimens.

Finally, the above methodology may be used as a tool for selecting or designing appropriate patient interventions including surgery, shape or size selection of a mandibular advancement splint and pressure waveforms for CPAP.

The above methodology illustrates how the mass of the tongue and soft palate can affect the collapse of the upper airway. Also, the direct effect of gravitational acceleration on sleep apnoea and obstruction in the upper airway can be evaluated. When the patient is positioned in the supine sleeping position, the deformation of the upper airway at the tongue base is significantly larger and a collapse time for soft, medium and hard stiffness anatomical parameters of the upper airway occurred in just under 1 s. However, when the patient is positioned in the prone sleeping position, no collapse was detected for any material combination and deformation was relatively low.

Thus, it is evident that the gravitational force and material stiffness anatomical parameters (which collectively define an upper airway tissue structural strength) have a significant effect in the Obstructive Sleep Apnoea.

The present disclosure also extends to a computer system configured to implement method 100 described above, such as system 200. It will be appreciated that method 100 may be formulated into instructions contained in a computer program. When executed by a computer, such as computer 205, the instructions cause the computer to carry out method 100. These instructions and the associated computer program may be stored on a computer-readable storage medium such that when the storage medium is inserted into and executed by a computer, the computer is instructed to carry out method 100.

It will be appreciated that the above methods provide for accurately modelling the complete upper airway as a single unitary model. This comprehensive modelling, including the nasal cavity in the model, is important as it generates more vortices that affect the generation of the negative pressure in the pharyngeal region and this increase the chance of collapse in this region. The present invention is able to model these vortices and their effect on the collapse of the upper airway for improved OSA prediction.

It will also be appreciated that the variability of anatomical parameters such as tissue properties with wakefulness state and patient position/orientation provides for a more 'living' model of a patient to be generated.

Interpretation

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Use of the terms "computer", "server" and the like in this specification may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Furthermore, the controller or processor may operate as a standalone device or may be connected, e.g., networked to other processor(s) and/or controller(s). In a networked deployment, the processor(s)/controller(s) may operate in the capacity of a server or a user machine in server-user network environment, or as a peer machine in a peer-to-peer or distributed network environment. The processor(s)/controller(s) may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Reference throughout this specification to "one embodiment", "some embodiments" or "an embodiment" means that a particular feature, structure or characteristic described in connection with the embodiment is included in at least one embodiment of the present disclosure and potentially multiple embodiments. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner. In this manner, when any methods described herein include several steps, no ordering of such elements is implied, unless specifically stated.

Thus, while there has been described what are believed to be the preferred embodiments and applications of the disclosure, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The claims defining the invention are as follows:

1. A method of simulating behaviour of an upper airway of a subject, the method including:
   receiving one or more tomographic images of the subject, the image including the subject's upper airway region captured at a predefined breathing state;
   generating, from the one or more tomographic images, a three dimensional geometric model of the upper airway region, the geometric model including a network of interconnected deformable mesh elements collectively defining:
      a fluid domain indicative of an interior of the upper airway region through which fluids are able to flow; and
      a solid domain indicative of an exterior of the upper airway region, the solid domain defining a single unitary model of the entire upper airway region segmented into a plurality of predefined geometric regions, each predefined geometric region being defined by one or more common anatomical parameters including tissue characteristics;
   performing a computer simulation on the geometric model to simulate behaviour of the upper airway region when the subject is positioned in a predefined position, the computer simulation including:
      performing a Computational Fluid Dynamics (CFD) analysis on the fluid domain;
      performing a Fluid-Structure Interaction (FSI) analysis between the fluid and solid domains under the influence of an applied gravity effect at a predefined direction through the geometric model corresponding to the predefined position; and
      outputting subject-specific parameters and/or a dynamic virtual airway model indicative of the behaviour of the upper airway region;
   wherein the method further includes:
   iteratively modifying one or more anatomical parameters of the geometric model by using the outputted subject-specific parameters and/or the dynamic virtual airway model as inputs to the geometric model, and
   simulating the behaviour of the upper airway region using the modified one or more anatomical parameters so as to assess the subject's response to a treatment regimen using a passive medical device.

2. The method according to claim 1 further including the step of assessing the subject's likelihood of a sleep disorder from the subject-specific parameters.

3. The method according to claim 1 further including the step of assessing the subject's response to a treatment regimen from the subject-specific parameters.

4. The method according to claim 1 wherein the predefined geometric regions include a tongue region having an associated mass anatomical parameter.

5. The method according to claim 1 wherein the anatomical parameters include a shape of a geometric region.

6. The method according to claim 1 wherein the predefined position includes a lateral left laying position or a lateral right laying position.

7. The method according to claim 1 wherein the predefined position includes a seated position.

8. The method according to claim 1 including the step of outputting a graphical representation of a simulated breathing cycle of the subject.

9. The method according to claim 1 wherein the behaviour of the upper airway includes a breathing performance of the subject.

10. The method according to claim 1 including the step of outputting a diagnosis of the subject based on the subject-specific parameters.

11. The method according to claim 1 including the step of outputting a suggested treatment solution or regimen of the subject based on the subject specific parameters.

12. The method according to claim 1 including the step of feeding the subject-specific parameters to a machine learning algorithm to generate revised anatomical parameters and feeding these revised anatomical parameters back as inputs to the geometric model.

13. The method according to claim 1 wherein the solid domain includes a region that is fixed in geometric space which corresponds to a posterior part of the upper airway that is attached to a subject's neck.

14. The method according to claim 1 including the steps of:
comparing the dynamic virtual airway model with real dynamic subject data to generate revised anatomical parameters; and
feeding the revised anatomical parameters back as inputs to the geometric model to generate a revised dynamic virtual airway model.

15. The method according to claim 1, further including the steps:
selectively modifying one or more of the anatomical parameters based on the subject-specific parameters;
repeating the method until one or more of the subject-specific parameters reach a predefined desired value; and
determining a treatment regimen for the subject based on the subject-specific parameters.

16. A computer system configured to implement a method according to claim 1.

17. A computer program comprising instructions which, when executed by a computer, cause the computer to carry out the method according to claim 1.

18. A computer-readable storage medium comprising instructions which, when executed by a computer, cause the computer to carry out the method according to claim 1.

19. The method according to claim 1 wherein the predefined geometric regions include a nasal cavity region and wherein the nasal cavity region forms part of the single unitary model of the solid domain for which the computer simulation is performed.

20. The method according to claim 1 wherein the anatomical parameters vary depending on a subject's wakefulness state and/or predefined position.

21. A method of simulating behaviour of an upper airway region of a subject, the method including the steps:
i. performing a computer simulation on a three dimensional geometric model of the upper airway region to simulate behaviour of the upper airway when the subject is positioned in a predefined position, wherein:
the geometric model is generated from one or more tomographic images of the subject, the image including the subject's upper airway region captured at a predefined breathing state; and
the geometric model includes a network of interconnected deformable mesh elements collectively defining:
a fluid domain indicative of an interior of the upper airway region through which fluids are able to flow; and
a solid domain indicative of an exterior of the upper airway region, the solid domain defining a single unitary model of the entire upper airway region segmented into a plurality of predefined geometric regions, each predefined geometric region being defined by one or more anatomical parameters including tissue characteristics;
ii. performing a Computational Fluid Dynamics (CFD) analysis on the fluid domain;
iii. performing a Fluid-Structure Interaction (FSI) analysis between the fluid and solid domains under the influence of an applied gravity effect at a predefined direction through the geometric model corresponding to the predefined position; and
iv. outputting subject-specific parameters indicative of the behaviour of the upper airway region;
wherein the method further includes:
v. iteratively modifying one or more anatomical parameters of the geometric model by using the outputted subject-specific parameters and/or a dynamic virtual airway model as inputs to the geometric model, and
vi. simulating the behaviour of the upper airway region using the modified one or more anatomical parameters so as to assess the subject's response to a treatment regimen using a passive medical device.

22. A method of assessing a subject's response to a treatment regimen for treating Obstructive Sleep Apnoea, the method including the steps:
a) before applying a treatment regimen to the subject:
i. receiving one or more tomographic images of the subject, the image including the subject's upper airway region captured at a predefined breathing state;
ii. generating, from the one or more tomographic images, a three dimensional geometric model of the upper airway, the geometric model including a network of interconnected deformable mesh elements collectively defining:
a fluid domain indicative of an interior of the upper airway region through which fluids are able to flow; and
a solid domain indicative of an exterior of the upper airway region, the solid domain defining a single unitary model of the entire upper airway region segmented into a plurality of predefined geometric regions, each predefined geometric region being defined by one or more anatomical parameters including tissue characteristics;

iii. performing a computer simulation on the geometric model to simulate behaviour of the upper airway region when the subject is positioned in a predefined position, the computer simulation including:
   performing a Computational Fluid Dynamics (CFD) analysis on the fluid domain;
   performing a Fluid-Structure Interaction (FSI) analysis between the fluid and solid domains under the influence of an applied gravity effect at a predefined direction through the geometric model corresponding to the predefined position; and
iv. outputting subject-specific parameters indicative of the behaviour of the upper airway;
v. iteratively modifying one or more anatomical parameters of the geometric model by using the outputted subject-specific parameters and/or the dynamic virtual airway model as inputs to the geometric model, and
vi. simulating the behaviour of the upper airway region using the modified one or more anatomical parameters so as to assess the subject's response to a treatment regimen using a passive medical device; and
b) applying a treatment regimen to the subject;
c) repeating steps a) i-vi on the subject; and
d) performing an assessment of the subject's response to the treatment regimen by comparing the subject-specific parameters before and after applying a treatment regimen.

23. A method of simulating behaviour of an upper airway of a subject, the method including:

receiving one or more tomographic images of the subject, the image including the subject's upper airway region captured at a predefined breathing state;
generating, from the one or more tomographic images, a three dimensional geometric model of the upper airway region, the geometric model including a network of interconnected deformable mesh elements collectively defining:
a fluid domain indicative of an interior of the upper airway region through which fluids are able to flow; and
a solid domain indicative of an exterior of the upper airway region, the solid domain defining a single unitary model of the entire upper airway region segmented into a plurality of predefined geometric regions including a nasal cavity region, each predefined geometric region being defined by one or more common anatomical parameters including tissue characteristics;
performing a computer simulation on the geometric model to simulate behaviour of the upper airway region including behaviour of the nasal cavity region when the subject is positioned in a predefined position, the computer simulation including:
performing a Computational Fluid Dynamics (CFD) analysis on the fluid domain;
performing a Fluid-Structure Interaction (FSI) analysis between the fluid and solid domains under the influence of an applied gravity effect at a predefined direction through the geometric model corresponding to the predefined position; and
outputting subject-specific parameters and/or a dynamic virtual airway model indicative of the behaviour of the upper airway region including the nasal cavity region.

* * * * *